United States Patent [19]

Liu et al.

[11] Patent Number: 4,747,407
[45] Date of Patent: May 31, 1988

[54] BLOOD VESSEL ANASTOMAT

[75] Inventors: Ying B. Liu; Heng W. Yang; Shu L. Ma; Shi Z. Liu; Nai H. Li, all of Chongqing, China

[73] Assignee: The Field Surgery Research Department of the Third Military Medical University, Chongqing, China

[21] Appl. No.: 869,867

[22] Filed: Jun. 2, 1986

[30] Foreign Application Priority Data

Sep. 3, 1985 [CN] China .................................. 85106639

[51] Int. Cl.$^4$ .............................................. A61B 17/04
[52] U.S. Cl. .............................. 128/334 R; 128/334 C; 128/303 R; 128/346
[58] Field of Search .......................... 128/334 R, 334 C

[56] References Cited

U.S. PATENT DOCUMENTS

| | | | |
|---|---|---|---|
| 2,965,900 | 12/1960 | Inokouchi | 128/334 R |
| 3,258,012 | 6/1966 | Nakayama et al. | 128/334 C |
| 4,073,179 | 2/1978 | Hickey et al. | 128/334 R |
| 4,233,981 | 11/1980 | Schomacher | 128/334 R |
| 4,350,160 | 9/1982 | Kolesov | 128/334 R |
| 4,467,804 | 8/1984 | Hardy et al. | 128/334 |
| 4,474,181 | 10/1984 | Schenck | 128/334 |
| 4,593,693 | 6/1986 | Schenck | 128/334 R |

Primary Examiner—Richard C. Pinkham
Assistant Examiner—Gary Jackson
Attorney, Agent, or Firm—Armstrong, Nikaido, Marmelstein & Kubovcik

[57] ABSTRACT

A kit for the anastomosing of a blood vessel which includes a pair of anastomic wheels. Each wheel has an axially extending hollow body for the passing of a blood vessel therethrough and a peripheral extending flange. The periphery of the flange has a plurality of forwardly extending pins for piercing and holding the wall of a blood vessel passing through the hollow body and stretched outwardly across the flange and impaled on the pins, the wheels with the blood vessel end impaled on the pins thereof being brought together with the flanges abutting and the projecting pins on the flanges being bent over the opposing flange with the stretched blood vessel wall therebetween to join the blood vessel walls. Also included are a hook and pressing needle for stretching and impaling the blood vessel ball on the pins; and clasping pliers for clasping the wheels and bending the pins.

11 Claims, 11 Drawing Sheets

BLOOD VESSEL ANASTOMAT

The present invention relates to blood vessel repair surgery, the implantation of blood vessel tissues and technical apparatus particularly to a blood vessel anastomotic device.

There are two procedures for blood vessel anastomosis: One by hand-suture and the other with anastomotic equipment. In the hand-suture method, blood vessel anastomosis can break the internal wall of the blood vessel, cause thrombosis and, hence, impeding the blood vessel. In addition, the hand-suture method is limited by suture thread, its operation is complicated and consumes time.

In the blood-vessel anastomosis equipment method, as comparing with the hand-suture method, better blood vessel anastomosis results. At present, blood-vessel anastomic equipment methods, generally are of two kinds, one is by amastomotic nail type blood-vessel anastomoses and the other by anastomotic ring type blood-vessel anastomosis.

The typical anastomotic nail type blood-vessel anastomoses was published in SURGICAL No. 73,902 1956, Japan. In this publication the blood-vessel anastomoses was provided with a U-type metallic nail. When used the U-type nail are located on the top semicircle of the anastomat head and are put into place by two anastomotic clamps separately on the anastomat. These clamps produce a propelling effort along the axle of the anastomosed blood vessel and push the propelling means of the anastomotic clamps in motion and cause the U-type anastomotic nails on the anastomat semicircle to pass through two layers of the blood vessel wall under the nails are plastically deformed into a ring shape to connect the two severed ends of the blood vessel tightly together.

In this method, because the six anastomotic nails on the blood walls are independent of each other, i.e. are, not join together, the anastomotic nails must be set one by one and this takes much time. This anastomat structure is complicate, is difficult to repair and is troublesome. Besides, the anastomosed blood vessel is connected by two layers of blood vessel walls. When the blood vessel is effected by tensile stress, the blood vessel wall produces certain contractive force, making the anastomosed opening to narrow, and easily forming thrombosis. Thus after the anastomosing the blood flow rate becomes low.

In another typical anastomotic wheel type anastomat which was published in the OPERATION magazine in 1962, in Japan, the anastomotic wheel is a metalic ring. There are six throughly drilled holes which are regular distributed on the responding ring surface. Between the holes there are six tied socketed needles. The anastomat is composed of a two pieces anastomotic clamps placed with an anastomotic wheel and one piece enclasped plier. When used, the two anastomotic wheels located separately on the circular ring of the anastomotic clamps, make the severed blood ends passing through the inner holes of the anastomotic wheels, turn over 90 degrees and hang up on the six sharp needles of the anastomotic wheel. Under the pressure from the enclasped plier, the two anastomotic clamps are closed together. The six needles of the anastomotic wheel plug into the six holes in the opposite anastomotic wheel. By bending the sharp tops of the needles, the needle tops are hung up on the side face of the holes on the opposite anastomotic wheel. The two severed blood ends are joined together. The anastomotic wheels function as a support frame for the severed ends of the blood vessel, dilating the anastomosed opening and the blood freely flow without forming thrombosis. However, because of the joining of the anastomotic wheels depends on the sharp ends of the six pair needle bending to hang up the hole wall end surface of the opposed anastomotic wheels, the needle end of the anastomotic wheel is very sharp and its tensil strength is rather low. It is easy for the blood vessel to slide. The joining of the anastomitic wheels by means of the needle sharp ends plugging into opposite needle hole, requires accuracy without any mistake, and very delicate technic to fabricate the anastomotic wheels. It complicates the operation and, at the same time, the variety of calibre of anastomotic wheel is limited. The anastomat depends on the elasticity of the clamp stem to tie in the two pieces of the clamp rods, which must be rather large. If used for surface surgery, it is inconvenient. After anastomosing, taking off the clamps, by loosing the clamp lock, applying sideward force and producing sideward swing, can loosen the blood-vessel opening which is already anastomosed, and enlarged the needle hole of the blood vessel wall. This increases the chances of blood vessel leak and thrombosis formation.

The prior-art blood-vessel anastomat which is similar to the above-stated two types of anastomat was disclosed as Japanese Pat. No. 70759 and No. 116451 (issued on June 12, 1981 and on Sept. 12, 1981). These two kinds of anastomats both are of the anastomatic wheel type. The structure of those apparatus are complicate and their operation is complex and consumming time.

U.S. Pat. No. 4,467,804 disclosed a anastomat having a pair of ring member for securement to the severed ends of blood vessel. The tubular members to be anastomosed and the ring members having annular connecting structure mate with each other to connect the ring members. The ring members are in a fixed relationship at a predetermined distance from each other. This structure is provided to connect the severed ends of the tubular member of the blood vessel contiguous to each other around the connecting structure to enable the ends to grow together at approximately the outer surface of the blood vessel tissues. This anastomat forms a foreign matter occupying space in the blood vessel and effects the blood flow rate. The anastomat can be fabracted in a variety of different sizes, however, because of its specific connecting structure, and the fabrication dimensions are limited and it can't be made in tiny sizes so that its availability is very limited.

In U.S. Pat. No. 4,474,181 (issued on Oct. 2, 1984), there published a kind of small blood vessel anastomat, which combines the hand-suture method and the anastomat ring method. This anastomat is a ring member type. The ring member has an interior surface with a diameter larger than that of the outer surface of the blood vessel. On the ring member there are at least three spaced-apart locations with a certain distance for tethering the blood vessel connecting suture thereto when such anastomat is in use, for disposing the ring around the severed ends of the blood vessel. The ends of the blood vessel are connected with at least three spaced-apart locations for suturing. The suture thread is tethered on the ring member to apply outward radial stress to the connected blood vessel. The stress in several directions helps to assure that, in the anastomosed blood vessel, the blood can flow freely. Because of this kind of device is for anastomosing small blood vessel, it can only be applied to blood vessel diameter of less than 1 mm. When stitching up the large blood vessel, the suturing space is limited and, the blood will seepage or leak and influence anastomosis results. This type of anastomat is not very adaptable.

In considering above mentioned prior-art with their special characters and disadvantages, the present invention provides a blood-vessel anastomat, having two anastomotic wheels, with assembling anastomotic clamps and pliers for clasping the anastomotic wheels. Hanging hook are provided for pulling or turning over the wall of blood vessel. The pressing needle for fixing firmly the wall of blood vessel after the blood vessel has been anchored onto the anastomotic wheel claws or needle ends. The disadvantages of above mentioned prior art are overcome to get best operation results.

The object of the present invention is to provide a simple blood vessel anastomat structure which is easy to fabricate and, its anastomotic wheel has the structure feature and appearance which are convenient for a punching process and can be mass produced.

The second object of the present invention is to provide a simple and reliable method with short consumming time during surgery which easily masters blood vessel anastomat. According to the present invention, when the anastomat is in use, the anastomotic wheels are deformed by clasping pliers into a permanent status by means of the plasticity of the material making up the anastomotic wheel. The sharp pins of the anastomotic wheels are bent into hooks and clasp the circular wall of the opposite anastomotic wheel in a stable and tight state. In general, a skillful operator can use this apparatus for finishing a anastomosis work in only about 5 minutes after trained of 1 or 2 weeks.

Another object of the present invention provides a kind of blood vessel anastomat which is agile in operation and reduces anastomosed blood vessel combine diseases. Due to the present invention the anastomotic clamp is locked by using a compression spring. The clamp occupies less space so that operation on surface surgery is more flexible. When used in deep surgery, lengthen handles are added onto the anastomotic clamps widening the range of the use of device. The anastomotic wheel of the invention has variety of calibres or diameters so that anastomosed blood vessel have a high rate of free blood flow. There is no foreign matter in the lumen of the blood vessel, and no stenosis in the anastomosed opening which can infect. More satisfactory results are obtained. The invention can also be applied to the following: blood vessel surgery repairing fields during wartime for the treatment of the war wounds trauma; the anastomosis of blood-vessel for the replantation of a severed limb; the implantation of an anastomosis blood vessel combination with blood-vessel pedicle tissue; anastomose the implantation of human interior organs as heart, lung, tongue and throat. It can also be used for anastomosing artifical blood vessel and reducing the combination diseases.

The detail description of the present invention and its attached reference drawings are explained as follows:

The preferred embodiment of the invention is a set of blood-vessel anastomat composed of several assemblies comprising:

A pair of anastomotic wheels, a pair of anastomotic clamps in which the anastomotic wheels are placed, a pair of pliers for clasping the anastomotic wheels together, several hooks and pressing needles for turning over the severed ends of blood vessel, anchoring the blood vessel to the wheels and fixing firmly the wall of blood vessel after the blood vessel has been anchored onto the anastomotic wheel claws. A pair of lengthened handles for the anastomotic pliers are provided for the operation of deep surgery.

Every assembly parts are disclosed with reference to the drawings as follows:

FIG. 3a is a front view of a pair of anastomotic pliers, the left side of the figure is the male clamp assembly, the right side is the female clamps assembly.

FIG. 3b is a side view of a pair of long plates of the anastomotic plier assembly, assembled at the inner side surfaces.

FIG. 3c is a vertical sectional view of the head portion of a pair of anastomotic clamps which have been joined together.

Figure 4A:
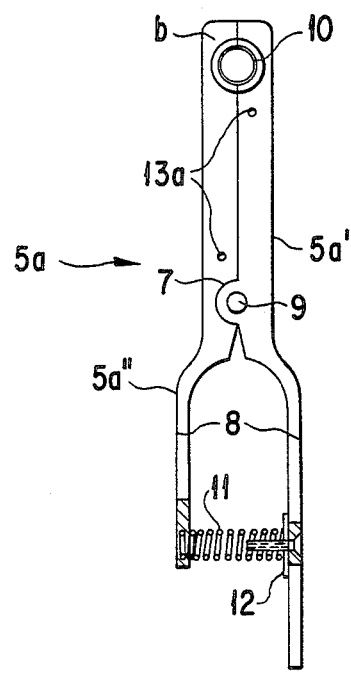
FIG. 4a shows an elevational view of the pressing needle according to the invention FIG. 4a' shows an elevational view of the pressing hook according to the invention.
Figure 4B:
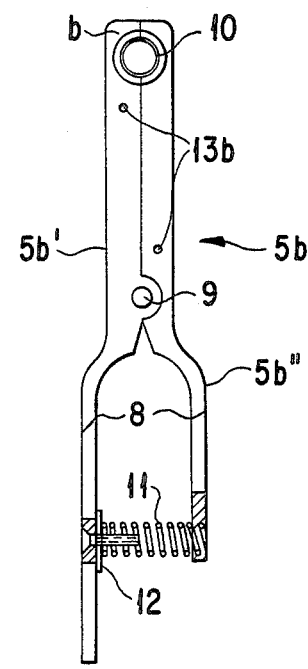
FIG. 4b shows a top view of the pressing needle of the invention.

FIG. 4b' shows a front view of the pressing needle of the invention.

FIG. 4c shows a front view of the hook according to present invention.

FIG. 4d is the front view of the anastomotic wheel clasping plier

FIG. 4d' is a side view of the anastomotive wheel clasping plier.

Figure 5:
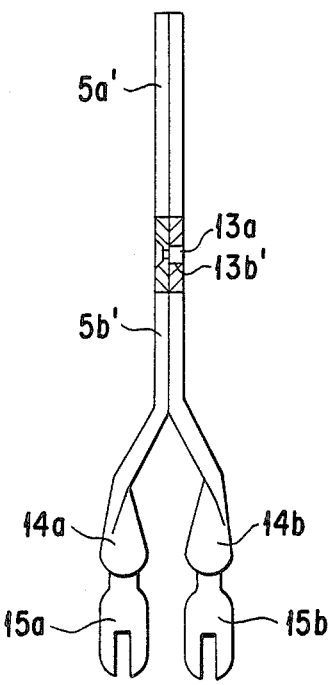

FIG. 5 is the front view a lengthened handle for the anastomotic clamp according to the present invention FIG. 5a is the side view of a lengthened handle for the anastomotic clamp according to the present invention.

Figure 6:
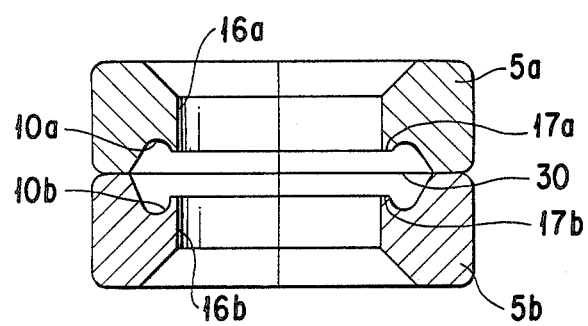

FIG. 6a shows the vertical sectional view of blood vessel anastomat according to the present invention, while the blood vessel is anastomosing and the anastomotic wheels have not been clasped yet.

FIG. 6b shows the vertical sectional view of blood vessel anastomat according to the present invntion, while the blood vessel is anastomosing and after the anastomosed.

Figures 7, 8, 9:
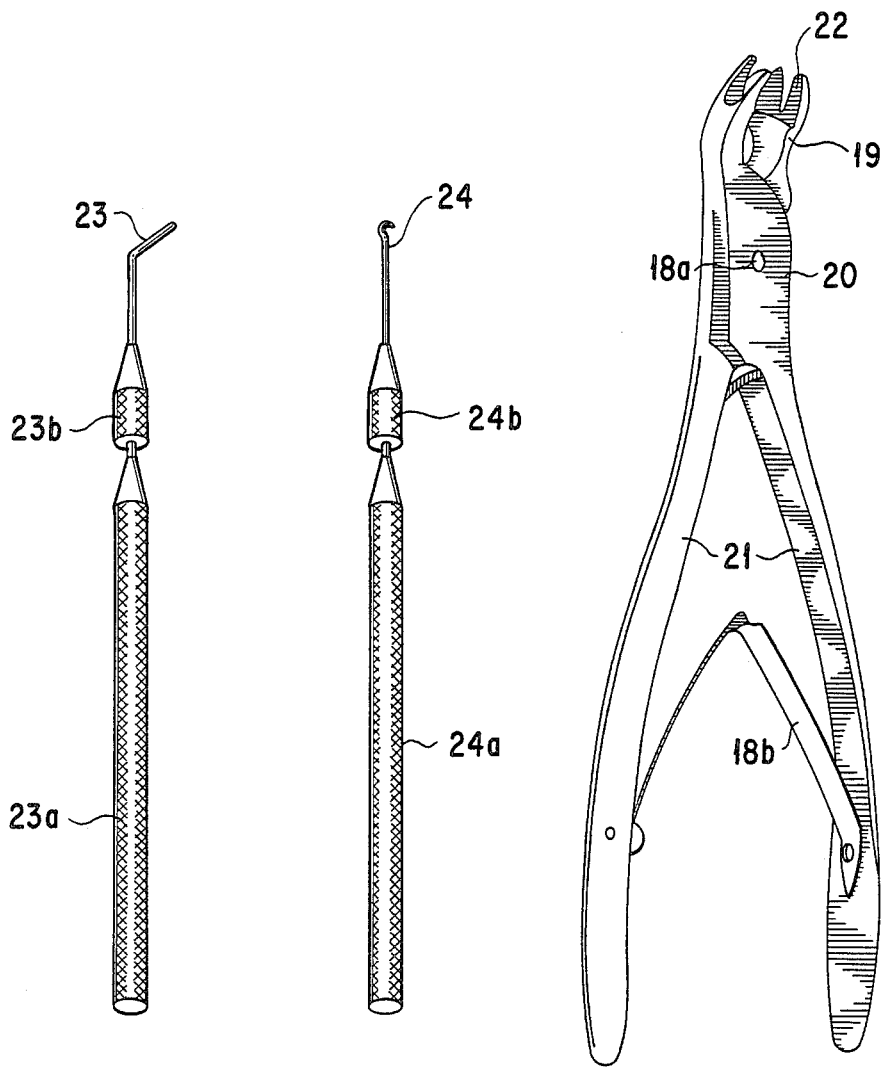
Figure 10:
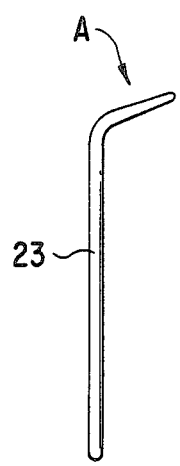
Figure 11:
Figure 12:
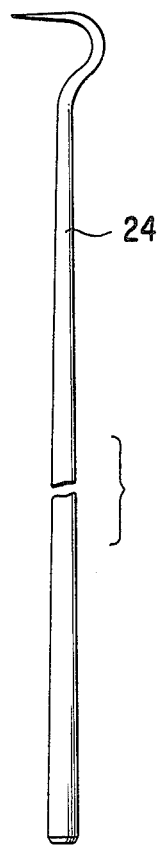
Figures 13, 14:
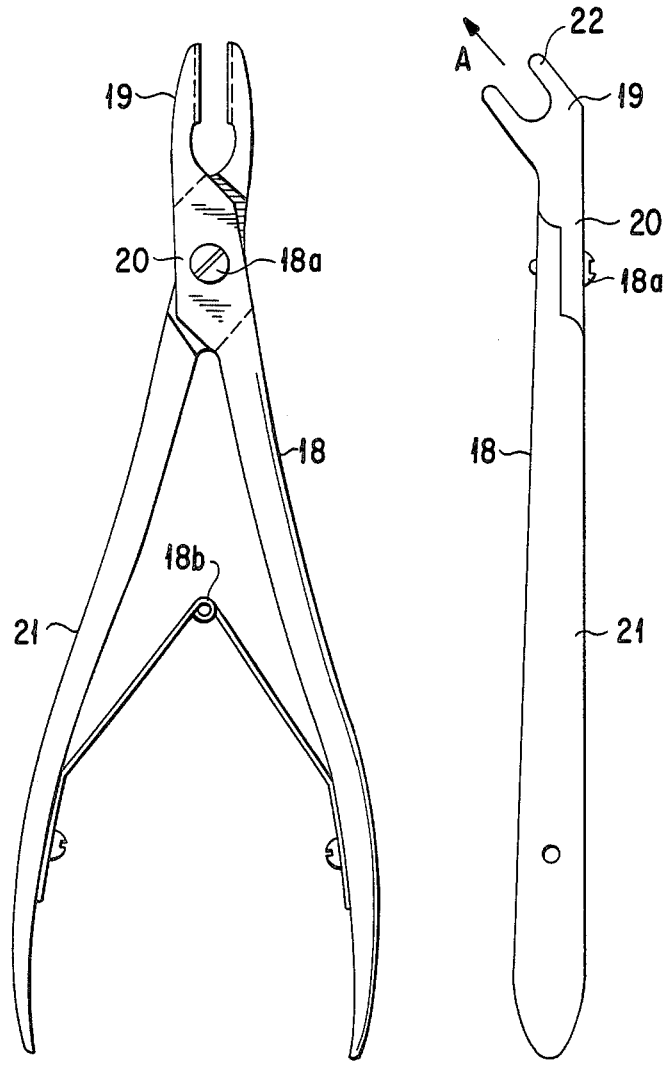
Figure 15:
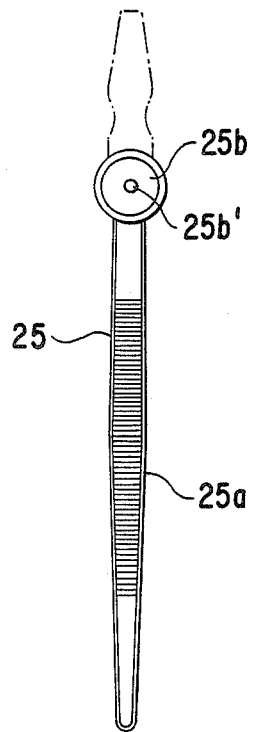
Figure 16:
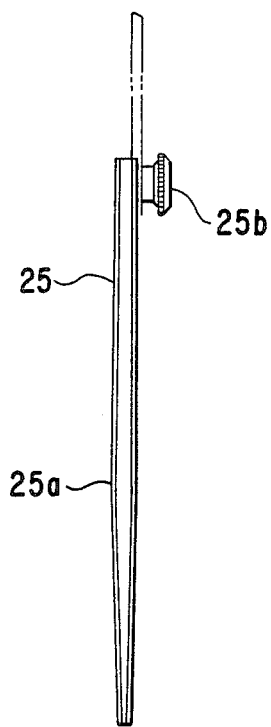
Figure 17:
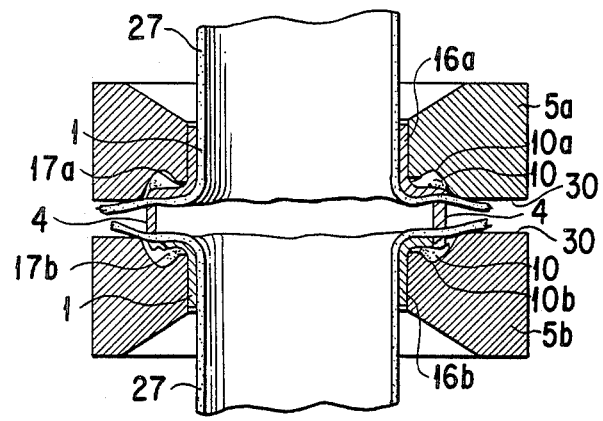
Figure 18:
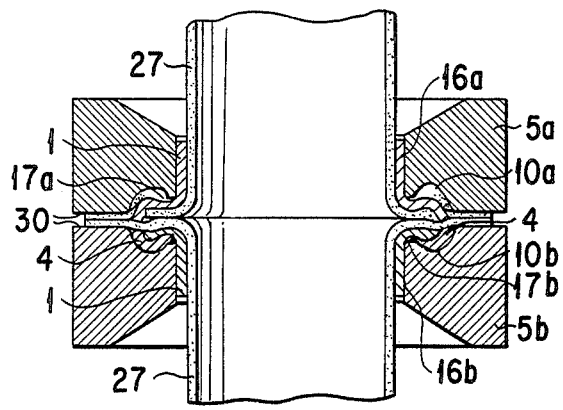
Figure 19:
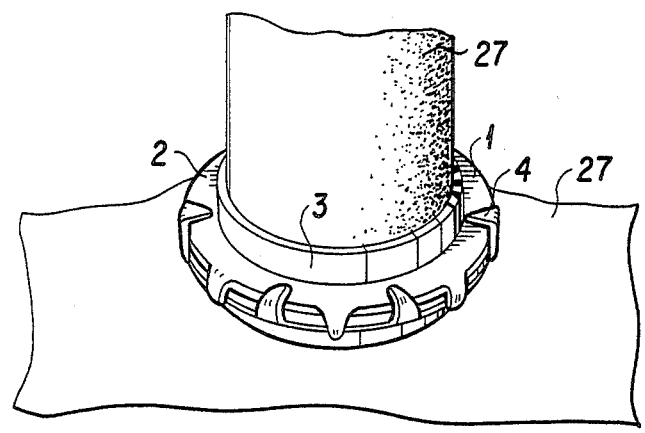

FIG. 7 shows a view of blood vessel end-side anastomosing according to the present invention.

According to above listed attached drawings, first of all the integration of the invented assembly parts should be explained.

Figure 1:
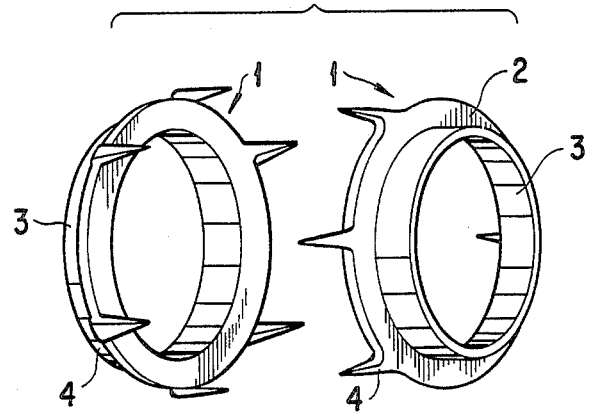
FIG. 1 shows an elevational view of a pair of anastomotic wheels according to the present invention.

Anastomotic wheel (1) a kind of metal circular wheel made by punching process, (cf. FIG. 1) is made with a circular ring surface (2) with a circle inner hole (3) and several sharp pins (4) symetrically distributed on the rim of the circular surface (2). The sharp pins (4) are bent into 90 degree angle with the circular surfaces. Each sharp pin is perpendicular to the inner hole (3) of the circular surface (2) and parallel to the wall hole. The end of sharp pin (4) is very sharp and connected to the circular surface (2) with rather wide root part with a width of about from 0.34 to 0.8 mm. The depth of circular surface (2), the wall of inner hole (3) and sharp pin all are from 0.25 to 0.3 mm. Thus, when the blood vessel is hung up on pins (4), by applying a larger pressure, it will be easier to hang up. As the tensile strength is at an equal condition, the contacted area between the wall of the blood vessel and the pins is larger, the pressure becomes smaller and the holes piercing through blood vessel wall are not easy to dilate or tear.

The circular surface (2) of anastomotic wheel, the inner hole (3) and the sharp pins (4) are made into one unit. Their separate functions are:

The circular surface (2) of anastomotic wheel, when under the pressure of the clasping pliers are clasped together. The sharp pins on anastomotic wheel are bent into hook-shape and clasped onto the circular surface (2) of the opposite anastomotic wheel as shown in FIG. 2.

The inner hole (3) receives the severed ends of blood vessel passing therethrough and the end of the blood vessel is turned outward over the sharp pins (4). The wall of the inner hole (3) is used for fitting anastomotic wheel (1) onto the circular groove of the head of the anastomotic clamp in which the anastomotic wheels are placed.

Figure 2:
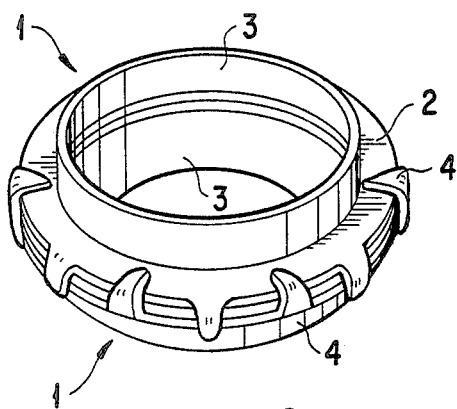
FIG. 2 shows a view of the anastomotic wheel which has been clasped.

The sharp pins (4) are used for hanging the severed ends of blood vessel, and for clasping the circular surfaces (2) of the opposite wheels (1), as shown in FIG. 2.

The anastomotic wheel (1) has another important feature. The inner side of the inner hole (3) toward the anastomosing plane of the circular surface (2) bending at an angle of 90 degree. The corner has a rather large filleted corner, FIGS. 6a, 6b and avoids damage to the inner wall of blood vessel.

Anastomotic wheel (1) is made of stainless steel or tantalum and titanium. These materials have better plasticity, good anti-corrosion property, are very light and and easy to fabricate. The anastomotic wheel (1) according to present invention can make at a variety of calipers with the range of diameter 1 to 30 mm. According to the caliper of blood vessel any suitable diameter of anastomosis wheel (1) can be selected for the anastomosis operation. Organic material and organic materials which can be dissolved by the body tissue after the blood vessel anastomosis are suitable for the anastomotic wheel and are within the scope of the present invention.

In order to adapt to the different calipers of a pair of anastomotic wheels (1), it is necessary to get a pair of anastomotic clamps (5a, 5b) that can be placed at the different calipers of the anastomotic wheel (1). The anastomotic clamps are the main instrument of blood vessel anastomat.

Figure 3:
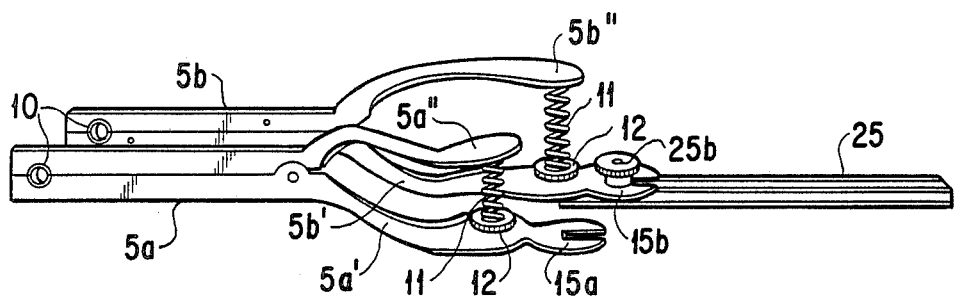
FIG. 3 shows a side-elevational view of a pair of anastomotic pliers.

Each pair of the anastomotic clamps (5a, 5b) is composed by a male clamp (5a) and a female clamp (5b), and each anastomotic clamp is made by a long plate and a short plate. (cf. FIG. 3a). In FIG. 3a, the left side is the male clamp (5a), the right side is the female (5b), FIG. 5b, are each divided into three sections: the head (6), the gill (7), and the handle (8). On the gill section, there is a gill axle (9) which combines respectively the long plate (5a') and the short plate (5a'') of the male clamp, the long plate (5b') and the short plate (5b'') of the female clamp, into one integral unit. The head section (6) of each clamp has a circular groove (10) in which the anastomotic wheels (1) are to be placed, the half of circular groove (10) lies on the long plate of the clamp, the other half on the short plate of the clamp. In addition, on the handle section (8) of the clamp is provided with a compression spring (11), one end of the spring (11) being fixed on the short plate of anastomotic clamp unit, namely (5a'') or (5b''), the other end of that being fixed on the long plate of the clamp through a adjustable screw (12) which can rotate in the direction of the short plate for compressing the spring (11). The reverse is true. By the elasticity of the compression spring (11) on the handle of the clamp, by pressing the two plates tightly together, the suitable caliper anastomotic wheel (1) can be placed in the circular groove (10) on the head section (6) of the anastomotic clamp and is firmly held. The spring (11) occupies very small space. While finishing the anastomosis and taking off the clamp for the blood vessel, a force perpendicular is applied to the clamps (5a, 5b) so as to avoid sideward swing and vibration and reduce damage to the wall of blood vessel and blood leak, as well as reducing the formation of thrombosis.

On each anastomotic clamp unit, the gill axle (9) is the rotation center and the connection for the long and short plates. The mutual contacting area is a plane.

There is a slight difference between the male clamp (5a) and the female one (5b). On the long male plate (5a'), near the circular groove (10) a fixed pin bolt (13a) is positioned, while on the short male plate (5a'') near the gill axle (9) another fixed pin bolt (13a) is positioned. Similarly, on the female clamp (5b), two pin holes (13a, 13b) are opened at the positions which are corresponding with the pin bolts (13a) of the male clamp (5a). When the anastomosis is preformed, the pin bolts (13a) of the male clamp into the pin holes (13b) of the female clamp (5b). Thus, the two anastomotic wheels (1) are acurately aligned to clamp wheels (1) and misalignment is avoided.

The long male plate (5a') at its lower section is made in a shape as: (cf. FIG. 3b) downward from pin bolt (13a) in the opposite direction tilting a certain degree of angle and extending a length of handle, then forming an angle of 90 degrees between the anastomotic plane and the handle (14a) of the long plate. The inner face of the handle (14a) is used for fixing the adjustable screw (12) of compression spring (11). The outside face of handle (14a) is used for putting pressure perpendicularly to the handle; the further extending at the lower end of handle 14a of long plate (5a') of male clamp, is formed on a swallowtail connector (15a) for insertion into the lengthen handle of anastomotic clamp which will be explained later.

The lower section of the short plate (5a'') of the male clamp is as above, but without any swallowtail connector.

Similarly, the long plate (5b') and the short plate (5b'') of female clamp have the same corresponding symetric structure as that of male clamp, the lower section of the long plate (5b') of female clamps has also a swallowtail connector (15b). When the male clamp (5a) is combined with the female clamp (5b), as shown in FIG. 3b, only the long plates of the male and female clamp can be seen.

Next to explain the structure of circular groove (10) on head section of anastomotic clamp, FIG. 3c shows a vertical sectional view of the head section of a pair of anastomotic clamps which have been joined together, but without the anastomotsed blood vessel therebetween.

As can be seen, in FIG. 3c the upper part of male clamp (5a), the lower part of female clamp (5b) have the inner holes (16a) and (16b) respectively with the same size diameters so as receive the hole wall of inner hole (3) of the anastomotic wheel (1) as the anastomosed blood vessel wall extends from the anastomotic clamp inner holes (16a, 16b) toward the anastomosed plane (30). The extended blood vessel ends pass through the beveled annular section (17a, 17b) of anastomotic clamps which just fit the circular surfaces (2) of anastomotic wheels (1) and contact each other and, hence, are suitable to place anastomotic wheel (1). The extended blood vessel ends pass toward the anastomosed plane (30) pass arc section (10a, 10b) making up the circular groove (10) in anastomotic clamp unit. The function of the arc will be explained later.

The anastomotic wheel clasping plier (18), as shown in FIG. 4, clamp the anastomotic clamps (5a, 5b) tightly for clasping the anastomotic wheels (1). Its structure as shown in the front view of FIG. 4d, has three sections: the head (19) the gill (20) and the handle (21). The left and right plate of the clasping plier (18) pass through the gill axle screw (18a) and connect together as a unit at the gill section. Handle sections (21) are connected by a band spring unit (18b); the head section (19) each has an opening fork (22, 22), FIG. 4d'. Each opening fork (22) is provided with two parallel arms, the joining section of two arms form a round arc-shaped opening. When the left and right plates are joined, the two fork arms with the corresponding side surfaces are perpendicular to the front view plane of clasping plier (18). The opposite surfaces of the fork arms are fabricated with embossing or threading, to avoid the plier sliding when clasping the clamps. The direction of the two fork arms as shown by arrow A, FIG. 4d' form an obtuse angle with the plier handle (21).

The connection section of two fork arms form a round arc-shaped opening for the blood vessel to pass through, and are of a caliper to suit the related size of anastomotic clamps (5a, 5b). Therefore, the clasping plier (18) can be made to a variety of specifications.

According to present invention the total length of clasping plier (18) is 17 cm.

According to the invention, the pressing needles (23) FIG. 4a and hanging hooks (24), FIG. 4a, are all the assembly parts for the anastomat.

The handle of pressing needle (23) is a cylindrical metal rod with its outer surface knurled for avoiding sliding. A center hole, longitudial to the axle of the rod, is used for the different calibre needles (23). Its top section is threaded for a screw nut (23b).

The screw nut (23b) is also made of a cylindrical metal rod and has a center hole with a longitudinal axis for fitting the different calibre of pressing needles (23) on handle 23a.

The top part of pressing needles (23) tilts a certain degree of angle with the handle (23a) (cf. FIG. 4b), on the top of the pressing needle (23) and has a pin hole (23') at the top of pressing needle. According to the different hole diameters of anastomotic wheel (1) and the width of sharp pins (4), a suitable hole diameter is provided on the pressing needle (23). After the wall of the blood vessel severed ends are turned over and hang up on sharp pins of the anastomotic wheel (1), the pressing needle (23) is used to press blood vessel wall and let the sharp pins (4) pass through the pin hole (23'). Thus, the wall of blood vessel tightly hangs up on the anastomotic wheel (1).

Hooks (24) are used when turning over the blood vessel and drawn the severed ends of blood vessel. The bended form is shown in FIG. 4c, and handle section (24a) and compression screw nut (24b) FIG. 4a' are similar in structure to corresponding parts of pressing needle 23.

As above mentioned, the lengthened handle (25) of anatomic clamp is composed of a rectangular handle (25a) and a compression screw nut (25b) located on the top end of the handle. The compression screw nut (25b) is screwed on a fixed bolt (25b'). When the anastomotic clamp lengthened handle (25) is used for deep surgery, the swallowtail connectors (15a) and (15b) of long plates of male and female clamps (5a', 5b') are inserted into two fixed bolts of lengthened handle (25a', 25b') which are then turned to fix the bolts, to carry out deep surgery.

Up to this time, the embodiment of the present invention which compose of blood vessel anastomat and its whole assembly parts has been explained one by one.

Hereafter, it is the description of the relationship between the assembly units or parts, and the way the blood vessel anastomat wheels.

When carry blood vessel anastomosis, the conventional condition of blood vessel and surgery instruments must be arranged and the anastomotic wheel (1) selected according to the caliper of the blood vessel. A pair of anastomotic wheel (1, 1) of the same diameter with the blood vessel caliper or with a difference not over 0.3 to 0.5 mm are selected and placed separately on the circular grooves (10, 10) of the male and female anastomotic clamps (5a, 5b). When this is done care must be taken so that the sharp pins (4, 4) of wheels (1, 1) do not coincide or align, but are staggered relative to each other. Next the severed ends of blood vessel (27, 27) are separately passed through the inner holes (16a, 16b) on the head section of male and female anastomotic clamps. The operator holds the hooks (24) turning the severed ends of blood vessel over 90 degrees of angle and hanging the blood vessel wall symmetrically on six sharp pins (4) of anastomotic wheel (1). The pressing pin (23) is then used to fix the hung up blood vessel on the pins. The clamps 5a, 5b with the blood vessel, thereon are aligned with each other by inserting fixed pin bolts (13a, 13a) on male clamp (5a) into pin holes (13b, 13b) on the female clamp (5b). Clamps (5a, 5b) are then drawn together, clasping plier (18) pressing tightly the head sections (6, 6) of the anastomotic clamps. Under the pressure of clasping plier (18), the two anastomotic wheels (1, 1) are gradually closed, as shown in FIG. 6a.

The six sharp pins (4) on each anastomotic wheel (1) pass through the wall of blood vessel which is between two sharp pins (4) of the opposite anastomotic wheel at the same time, pins (4) begin to bend along the circular arc (10a or 10b) of circular grooves (10) of the opposite anastomotic clamp (5a 5b). As the pressure applied for clamping is over the limit of elasticity of the material in anastomotic wheel (1), the sharp pins (4) are deformed into a permanent status and clasped each other on the circular surface (2) of the opposite wheel (1). Thus, the two severed ends of blood vessel are clasped tightly together as shown in FIG. 6b.

Besides, using the present invention of anastomat, can also make the operations of blood vessel end-side anastomosis, as shown in FIG. 7.

The present invention, the blood vessel anastomat, compared with the prior art has many advantages as follows:

1. The pair of anastomotic wheels (1) according to present invention are clasped mutually by means of the sharp pins (4) after receiving the pressure and bending into nearly semi-ciruclar, and then clasping onto circular surface (2) of the opposite anastomotic wheel; therefore, it has high anti-tensile strength and the anastomosed blood vessel does not leak.

2. On account of the wheel claw or sharp pins (4) of anastomotic wheels (1) being clasped on the opposite wheel in between two sharp pins (4); it allows of a longer distance for displacement and raises the rate of successful operation and shortens operating time.

3. Because of high anti-tensile strength of the anastomotic wheel it can be applied in larger blood vessel anastomosing.

4. Due to the sharp pins width of the anastomotic wheel which are much wider than that of the known anastomotic wheel, the pin holes piercing piercing through the blood vessel wall are not easy to dilate or to be torn.

5. Due to the filleted corner of the wheel (1) where the blood vessel outer wall is turned over an angle of 90 degrees outward, damage to, the outer membrane of blood vessel is avoided.

6. In the present invention the anastomotic clamps use compression spring (11) to lock tightly the long and short clamp plates. Such plates are loosened by perpendicular force. Thus, sideward swing and vibration are avoided and the chances of producing blood leak and the formation of thrombosis is reduced.

7. According to the present invention not only the anastomotic wheel is light and delicate which is suitable for punching fabrication and can be mass produced, but also the anastomotic clamps (5a, 5b) using the compression spring (11) occupy small space, and have better adaptability.

8. In the anastomat of the present invention, the operation results are nice and satisfactory. Also due to the anastomosed plane (30) between the two anastomotic wheels (1, 1) there exists a certain safety clearance after anastomosing.

The above description has explained completely about the very important advanced characteristics of this invention, but the inventor still considers: that there still exists some things to be improved, for example, when using in chest and abdomen blood vessel anastomosis surgery, the lengthened handle of anastomotic clamp must be changed into a bent shape; the changing of the calibres of anastomotic wheels; using absorbent material instead of anastomotic wheel; the other accessories to be changed in forms, improved and variated such as the hooks, the pressing needle etc. are all within the scope of improvement of the present invention.

We claim:

1. A blood vessel anastomat kit for blood vessel repair surgery for the anastomosing of a blood vessel, comprising a pair of anastomotic wheels, each of said wheels having an axially extending circular hollow body, a flange extending perpendicular at one end of said body and circumferentially and peripherally around said one end and a plurality of equally spaced short pins around the periphery of said flange and extending axially and forwardly from said flange and said body; a pair of anastomotic clamps for receiving said anastomotic wheels, each of said clamps having a pair of plates hinged together intermediate their ends, said plates at one end of said clamp each having one half of a circular groove member abutting with the other half of the circular groove member in the other of said plates in said clamp when said clamp is closed and forming therein and therebetween a clamp for receiving and retaining one of said anastomotic wheels with the axis of said wheel perpendicular to the direction said plates of said clamp are hinged to each other; at least one hook and at least one pressing needle for engaging and turning the end of a blood vessel passed through said axially extending circular hollow body of said anastomotic wheel, for deflecting said end outwardly over said perpendicular flange, for engaging said deflected end with said pins and for piercing and engaging said deflected end on said pins; an anastomotic wheel clasping plier for clasping said circular groove members on said clamps with said anastomotic wheels retained therein and said deflected ends of said blood vessel pierced and engaged on said pins and for deflecting the ends of said pins on said anastomotic wheels outwardly and around said perpendicular flange of the other of said wheels for clasping said anastomotic wheels and said ends of said blood vessels together; and a pair of lengthened handles for said anastomotic clamps.

2. A blood vessel anastomat kit as claimed in claim 1, characterized in that said anastomotic wheel is a metallic circular wheel which comprises a circular inner wall forming said axially extending circular hollow body, said hollow body being open at its axial ends, and a plurality of sharp pins uniformly and symmetrically distributing on the periphery of said flange, said sharp pins being bent into 90 degrees angle to the surface of said flange when said anastomat is assembled.

3. A anastomotic wheel as claimed in claim 2, characterized in that said circular wheel, said flange and said sharp pins are a punch fabricated unit.

4. A anastomotic wheel as claimed in claim 2, characterized in that said sharp pins each has a root section width between 0.34 and 0.8 mm and are connected on the outer rim of said flange; the number of said sharp pins being not less than 4 and not more than 6.

5. A anastomotic wheel as claimed in claim 2, characterized in that said circular inner wall of said anastomotic wheel and said flange form an angle of 90 degrees at the junction between said circular inner wall and said flange.

6. A anastomotic wheel as claimed in claim 2, characterized in that said anastomotic wheel is made of a metal selected from the group stainless steel, tantalum titanium and alloys thereof.

7. A blood vessel anastomat clamp as in claim 1, wherein said anastomotic wheel clasping plier is composed of left and right plier pieces, and are connected into one integral unit at gill section by gill axle screw; the handle section of said clasping plier connects with a band spring means; and the head section of said plier has a fork opening forming an obtuse angle with said plier handle, and the clasped plane of said plier is perpendicular to the front view plane of said plier.

8. A blood vessel anastomat as claimed in claim 1, wherein said anastomotic clamps comprise a male clamp and a female clamp, each clamp being composed of a long and short plate said long and short plates of each clamp combined into one integral unit by a gill axle at gill section forming said plates, each of said clamps has a head section with a circular groove for receiving said anastomotic wheel, a handle section on each of said clamps, said handle section having a compression spring, one end of said spring being fixed on said short plate of said clamp, the other end of said spring being fixed on said long plate of the clamp through an adjustable screw.

9. A anastomotic clamp as claimed in claim 8, characterized in that said male clamp is provided with two pin bolts and said female clamp is provided with two pin holes, the ends of said long plates of said clamps having a swallowtail connector.

10. A anastomotic clamp as claimed in claim 8, characterized in that said circular groove for receiving said anastomotic wheel is formed for passing a blood vessel wall through said circular inner wall of said anastomotic wheel into said inner hole of said anastomotic clamp, and extends toward an anastomotic plane through a level annular section and an arc section to said anastomotic plane.

11. A blood vessel anastomat claimed as in claim 8, wherein a lengthened handle is attached to said long plate of each of said anastomotic clamps, said lengthened handle having a compression screw nut located on the top end of said handle which nut threads on a fixed bolt; on said lengthened handle for fixing said lengthened handle to said long plate of said clamp.

* * * * *